(12) United States Patent
Geneve et al.

(10) Patent No.: US 7,621,917 B2
(45) Date of Patent: Nov. 24, 2009

(54) BONE RECOVERY DEVICE

(75) Inventors: Eric Geneve, Sallanches (FR); Johan Bejeannin, Gieres (FR); Hervé Richard, Notre Dame de Bellecombe (FR)

(73) Assignee: Anthogyr, Sallanches (FR)

( * ) Notice: Subject to any disclaimer, the term of this patent is extended or adjusted under 35 U.S.C. 154(b) by 1037 days.

(21) Appl. No.: 10/990,610

(22) Filed: Nov. 17, 2004

(65) Prior Publication Data

US 2006/0106353 A1  May 18, 2006

(51) Int. Cl.
*A61F 5/00* (2006.01)
(52) U.S. Cl. .................................................. 606/86 R
(58) Field of Classification Search ................. 600/562, 600/564, 565, 570, 571; 606/86, 114, 115, 606/127, 128; 210/94
See application file for complete search history.

(56) References Cited

U.S. PATENT DOCUMENTS

| | | | | |
|---|---|---|---|---|
| 4,553,553 A | * | 11/1985 | Homann et al. | 600/562 |
| 4,685,472 A | * | 8/1987 | Muto | 600/573 |
| 4,834,703 A | * | 5/1989 | Dubrul et al. | 604/48 |
| 5,244,458 A | * | 9/1993 | Takasu | 604/22 |
| 5,275,609 A | * | 1/1994 | Pingleton et al. | 606/170 |
| 5,766,134 A | * | 6/1998 | Lisak et al. | 600/562 |
| 6,022,354 A | * | 2/2000 | Mercuri et al. | 606/80 |
| 6,299,763 B1 | | 10/2001 | Ashman | |
| 6,406,454 B1 | * | 6/2002 | Hajianpour | 604/48 |
| 6,908,455 B2 | * | 6/2005 | Hajianpour | 604/266 |
| 7,204,810 B2 | * | 4/2007 | Hynes et al. | 600/562 |
| 7,214,059 B2 | * | 5/2007 | Takahashi | 433/92 |

\* cited by examiner

*Primary Examiner*—Thomas C Barrett
*Assistant Examiner*—Nicholas Woodall
(74) *Attorney, Agent, or Firm*—William H. Eilberg

(57) ABSTRACT

The bone recovery device of the invention comprises an axial main body with an axial cavity passing through it, a front connector incorporating an axial passage and adapted to be fixed to the main body, a filter with a tubular filtering wall adapted to be fitted into the main body, and a scraper piston that slides inside the filter. The scraper piston blocks the end of the filter, and a radial outlet is provided in the axial main body, with an annular cavity left free around the filter between the filter and the axial main body. A canula is inserted into the distal end of the filter. The recovery device may therefore be used to recover bone retained by the filter during aspiration through the canula by the radial outlet, and bone fragments may be extracted by sliding the piston and withdrawing the canula. The recovery device may therefore be used several times without demounting it.

12 Claims, 3 Drawing Sheets

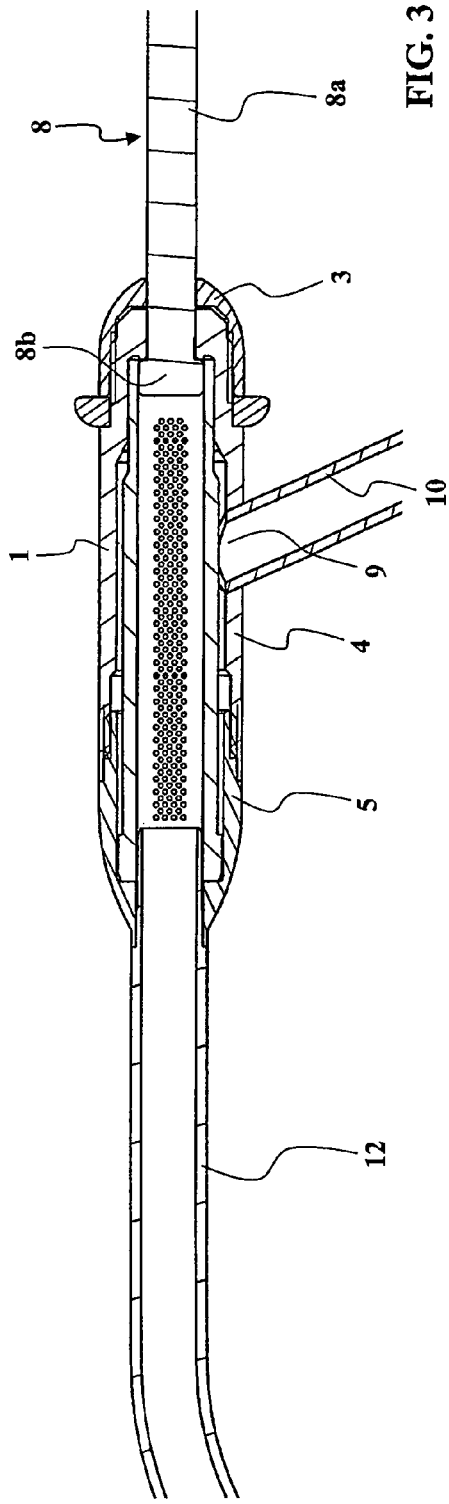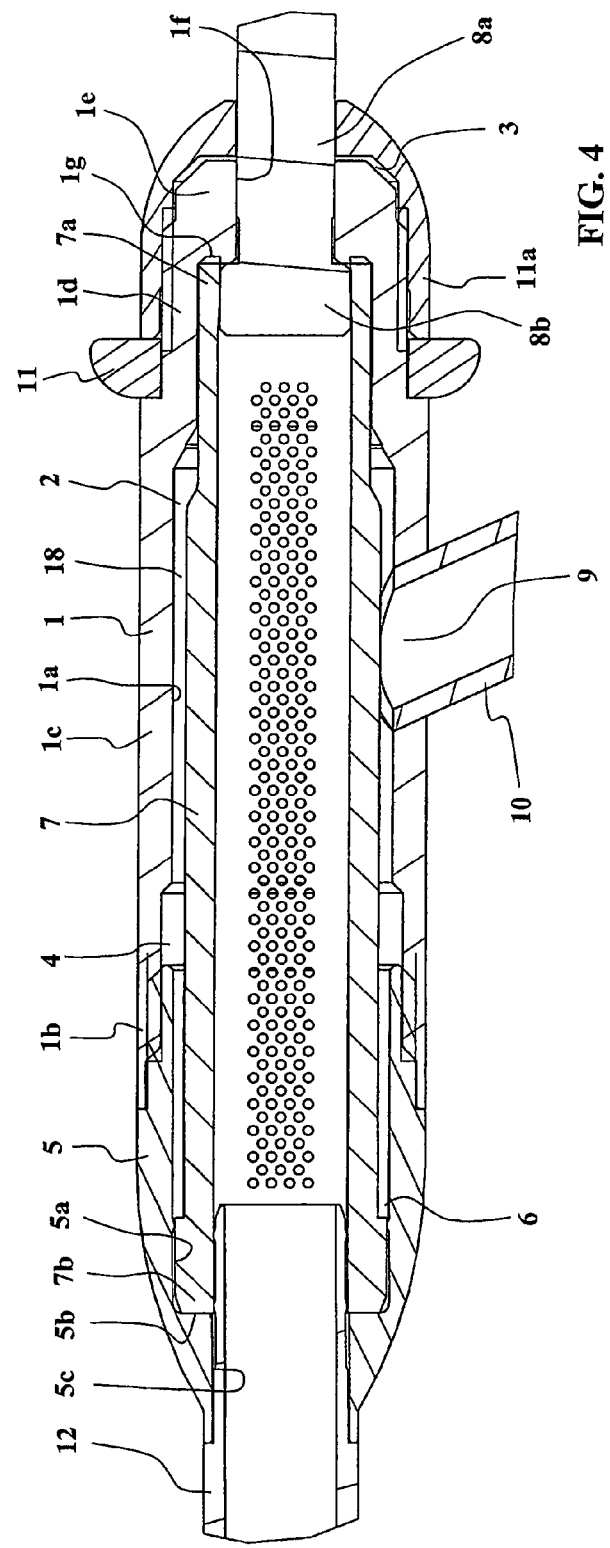

BONE RECOVERY DEVICE

BACKGROUND OF THE INVENTION

In surgery, especially when fitting dental implants, practitioners are often confronted with a requirement for bone material to be used for backfilling. Backfilling ensures good retention of an implant or contributes to the esthetic aspects of the practitioner's work.

In practice, this refers to carrying out bone micrografts.

Self-grafting is recommended to prevent rejection of the graft. To this end, bone is taken from the patient and reimplanted directly during the intervention, with minimum handling.

Practitioners usually attempt to recover as much bone material as possible from the drills and other tools used. This is not always effective, and the volume of bone recovered is not always sufficient.

In some circumstances, if the quantity of bone recovered is insufficient, synthetic bone backfilling materials may be used. Such materials, although developed for this specific purpose, do not guarantee so readily the absence of graft rejection.

During dental surgical interventions, while the practitioner is working in the mouth, an assistant is responsible for aspiration of saliva and debris present in the mouth. This aspiration is effected using canulas connected to the standard suction system of the dentist's chair. Thus, during drilling operations, bone debris are aspirated and lost in the general filtration system of the dentist's chair.

Recovery systems using filters have already been envisaged for increasing the quantity of bone recovered. For example, U.S. Pat. No. 6,299,763 describes a device of this kind, comprising a main body which has an axial cavity passing through it that has a proximal end and a distal end, and comprising a front connector that has an axial passage through it and is fixed to the distal end of the main body. A filter with a filtering wall of generally cylindrical tubular shape may be fitted into the main body and held coaxially therein. An annular cavity is left free around the filter between the cylindrical filtering wall of the filter and the internal lateral faces of the axial main body and the front connector. In the recovery position, a proximal stopper shuts off the proximal end of the filter, and forces the liquid to pass radially through the wall of the filter and then to flow around the stopper to exit via an axial outlet.

In the above device, bone fragments are collected inside the filter during the recovery step, by virtue of aspiration of the fluids from the axial outlet.

The bone must then be recovered. In the above prior art device, this requires separation of the axial main body and the front connector, extraction of the filter and its stopper, and then insertion of the distal end of a scraper piston, removal of the stopper and movement of the scraper piston toward the proximal end to propel the bone fragments toward the proximal end.

This requires relatively complex manipulations and in particular demounting of the device, which does not guarantee satisfactory hygiene. Moreover, there is no provision for replacing the filter conveniently and satisfactorily in the device to carry out a plurality of successive bone recovery operations on the same patient. The recovery capacity is therefore limited.

SUMMARY OF THE INVENTION

An object of the present invention is to avoid the drawbacks of prior art bone recovery devices by proposing a new structure that assures effective bone recovery and allows a plurality of successive uses by emptying the filter several times and returning it to an aspiration position without demounting it. As a result, hygiene conditions may easily be complied with whilst the recovery capacity and the ease of use are considerably increased.

To achieve the above and other objects, the invention proposes a bone recovery device for recovering bone fragments during surgery, comprising:

a front canula, an axial main body having an axial cavity passing through it with a proximal end and a distal end, a front connector incorporating an axial passage and adapted to be fixed to the distal end of the main body, a filter having a filtering wall of generally cylindrical tubular shape and adapted to be retained in position in the main body, an annular cavity left free around the filter between the cylindrical filtering wall of the filter and internal lateral faces of the axial main body and the front connector, in which device:

the main body comprises a radial outlet communicating with the annular cavity and adapted to be connected to a suction device, and a scraper piston is provided, having a piston rod that passes through the proximal end of the main body, and having a piston head adapted to slide axially inside the cylindrical tubular filter, the piston head blocking the proximal end of the filter at all times during use of the bone recovery device during a recovery phase and emptying the filter on axial movement in translation toward the distal end.

Thanks to the radial position of the outlet, the scraper piston may remain permanently in the axial main body, for a plurality of successive axial sliding movements. Thus, the bone recovery device may be used a first time in a recovery position, after which the filter is emptied by moving the scraper piston and the scraper piston returned to the recovery position for a new bone recovery step, without demounting the filter or the piston.

During a complete intervention, the system of the invention enables a plurality of "recovery-application" phases to be carried out without special manipulation. The piston may be returned to the recovery position by simple rearward actuation. This enables the filter to be emptied several times if it fills up or if there are several implants to be fitted.

One advantageous embodiment of the bone recovery device comprises a removable front canula adapted to be fitted to the front connector to communicate with the axial passage and the interior of the filter.

The device claimed preferably comprises end of travel abutment means for limiting movement in translation of the piston head beyond the proximal end of the filter.

The filter may advantageously be retained in the axial main body by virtue of its proximal and distal end regions abutting against the axial main body and the front connector, respectively.

This constitutes a simple way both to retain the filter in the axial main body and to free up the annular cavity around the filter.

The front connector may advantageously be removable, for example its proximal end may be screwed onto or into the distal end of the axial main body.

Thus the device may be demounted to separate the front connector from the axial main body and to extract the filter.

The diameter of the axial passage in the front connector is preferably substantially the same as the inside diameter of the filter. As a result, a canula may be inserted axially and at the same time into the front connector and into the distal end region of the filter. This also facilitates emptying the filter by sliding the piston after removing the canula.

All the components of the bone recovery device are preferably demountable to facilitate cleaning and/or decontamination and/or sterilization.

The bone recovery device of the invention may advantageously comprise a suction device connected to the radial outlet of the axial main body.

BRIEF DESCRIPTION OF THE DRAWINGS

Other objects, features and advantages of the present invention will emerge from the following description of particular embodiments of the invention, given with reference to the appended drawings, in which:

FIG. 3 is a side view in longitudinal section of the FIG. 1 bone recovery device in a recovery configuration; and FIG. 4 is a side view to a larger scale of the central portion of FIG. 3.

DESCRIPTION OF THE PREFERRED EMBODIMENTS

Figure 1:
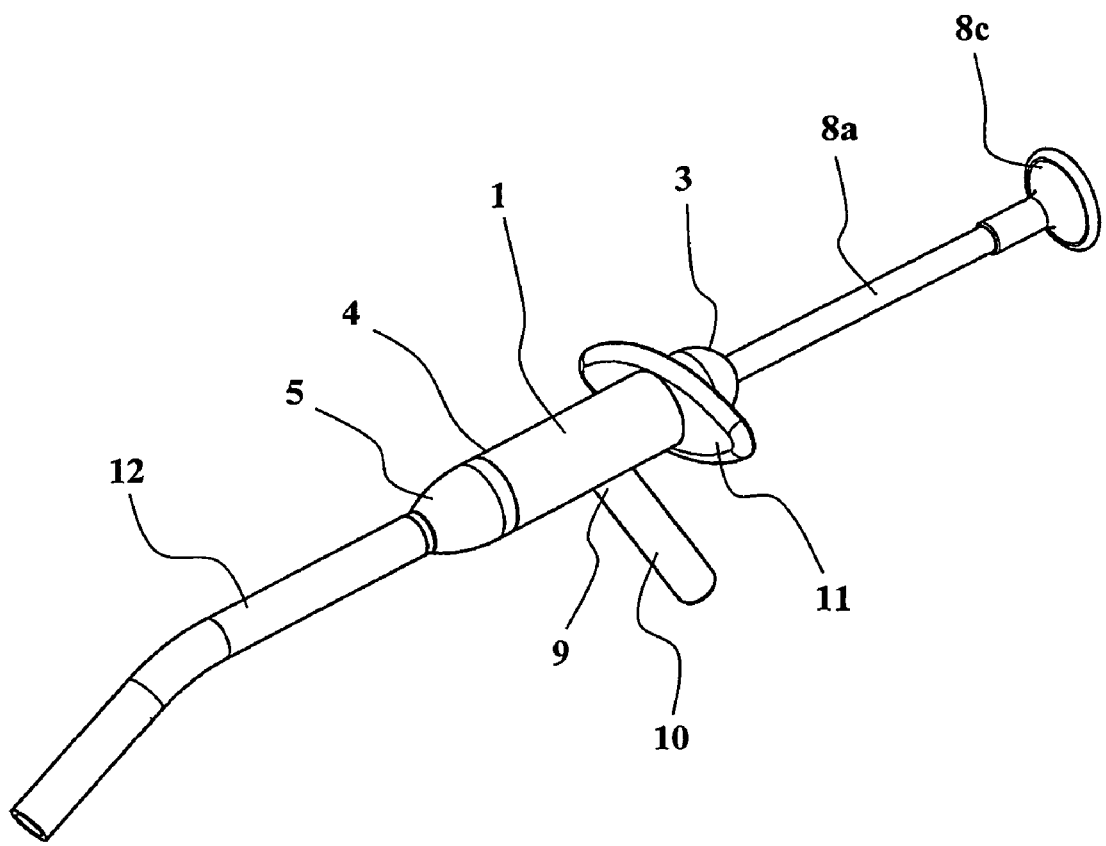
FIG. 1 is a general perspective view of one embodiment of a bone recovery device of the present invention.
Figure 2:
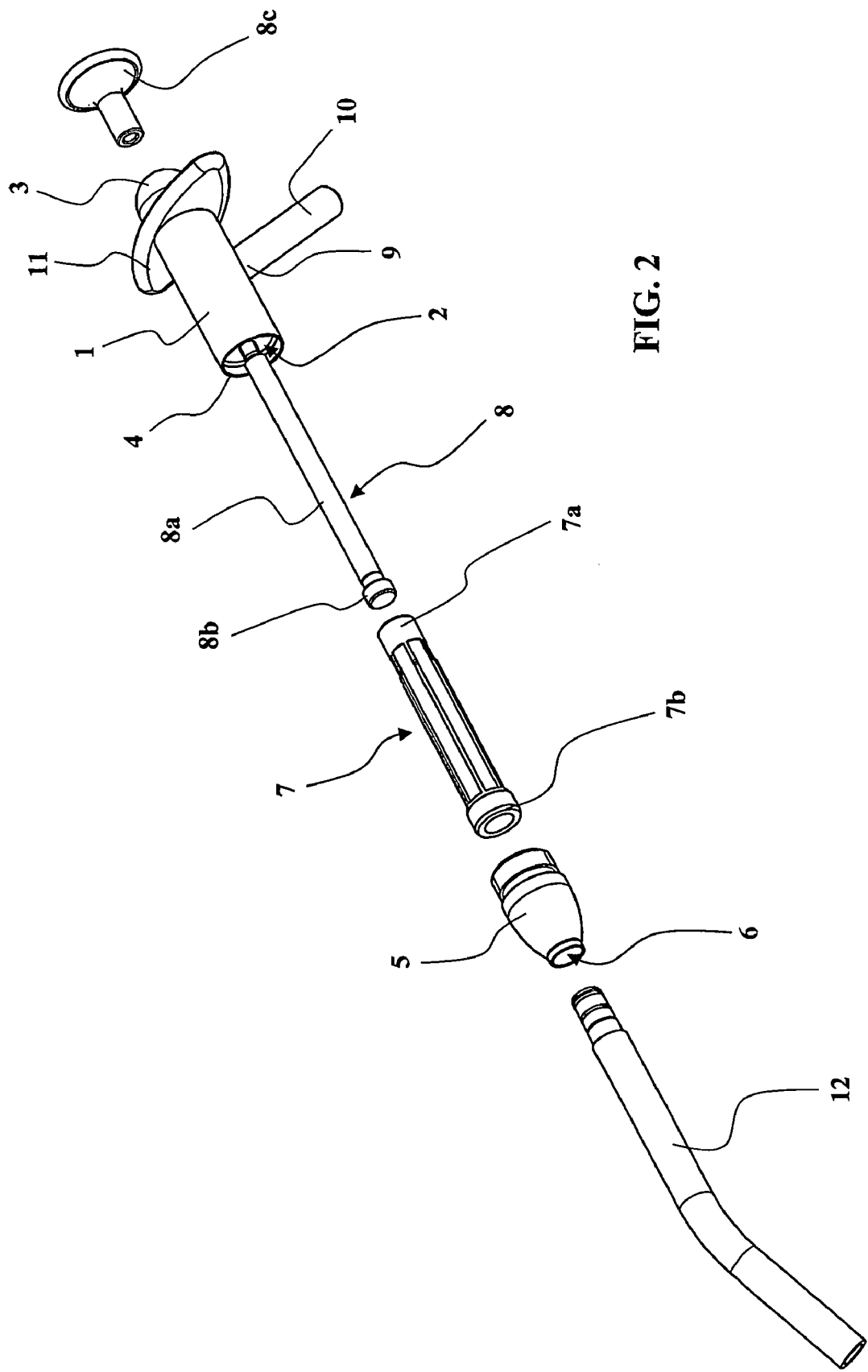
FIG. 2 is an exploded view of the main components of the FIG. 1 bone recovery device.

The embodiment of a bone recovery device of the invention shown in the figures comprises an axial main body 1 having an axial cavity 2 passing through it with a proximal end 3 and a distal end 4.

A front connector 5 incorporating an axial passage 6 is fixed to the distal end 4 of the main body 1. In practice, the proximal end of the front connector 5 may be screwed into the distal end 4 of the axial main body 1.

A filter 7, with filtering walls of generally cylindrical tubular shape, may be fitted into the main body 1 and into the front connector 5. The proximal end region 7a and the distal end region 7b of the filter 7 hold it centered and abutted against the axial main body 1 and the front connector 5, respectively. An annular cavity 18 is left free around the filter 7 between the cylindrical filtering wall of the filter 7 and the respective internal lateral faces 1a and 5a of the axial main body 1 and the front connector 5.

In practice, the axial main body 1 may comprise a threaded distal section 1b for fixing the front connector 5, a central section 1c having a bore of greater diameter than the filter 7 to define the annular cavity 18, a fixing section 1d having a smaller diameter that is substantially equal to the outside diameter of the filter 7 for retaining the proximal end 7a of the filter 7, and a proximal section 1e whose bore if has a smaller diameter and is connected by a shoulder 1g to the bore of the fixing section 1d.

The bone recovery device further comprises a scraper piston 8, having a piston rod 8a that passes through the proximal end 3 of the main body 1, and having a piston head 8b adapted to slide axially in the cylindrical tubular filter 7.

Accordingly, by actuation of the piston rod 8a, the piston head 8b may be slid in the filter 7 between its proximal end 7a and its distal end 7b.

In the bone recovery position, the piston head 8b is near the proximal end 7a of the filter 7, for example abutted against an abutment that limits its travel.

In practice, the piston head 8b may be an added head screwed to the distal end of the piston rod 8a whose proximal end may receive a proximal pusher head 8c. Alternatively, the piston rod 8a and the piston head 8b may be in one piece.

The axial main body 1 further comprises a radial outlet 9 that communicates with the annular cavity 18, and may comprise an outlet tube 10. The outlet tube is fixedly or removably connected to the radial outlet orifice 9. An outlet tube 10 welded to the axial main body 1 may be preferred.

The axial main body 1 further comprises radial gripping raised portions 11 in its proximal end region. Thus the user may get a grip between the radial gripping raised portions 11 and the pusher head 8c in order to push in the piston. With radial gripping raised portions 11 and a pusher head 8c of sufficient size, as shown in the figures, the device resembles a syringe and facilitates bone placement.

In the embodiment shown in the figures, the bone recovery device of the invention further comprises a removable canula 12 adapted to be fitted to the front connector 5 to communicate with the axial passage 5a and with the interior of the filter 7.

In practice, the axial passage of the front connector 5 may advantageously comprise a proximal bore 5a whose diameter is substantially the same as the outside diameter of the filter 7, and which joins via a shoulder 5b to a distal bore 5c whose diameter is substantially equal to the inside diameter of the filter 7. As a result, the canula 12 may penetrate the distal bore 5c and the distal portion of the interior passage of the filter 7, with the filter 7 held correctly in its distal end region 7b by the shoulder 5b and the proximal bore 5a of the front connector 5. At the same time, the filter 7 is held correctly in its proximal end region 7a by the shoulder 1g and the bore of the fixing section 1d.

The operation of the bone recovery device is as follows:

In its recovery position, shown in the figures, the piston head 8b blocks the proximal end 7a of the filter 7. A suction device, such as those usually provided on dentist's chairs, for example, and not shown in the figures, is connected to the radial outlet 9 and the canula 12 is placed in the mouth of the patient. Thus the recovery device of the invention is connected to the suction line, instead of an ordinary canula. The canula 12 aspirates fluids from the mouth that entrain bone fragments which collect inside the filter 7, whereas liquid passes radially through the filtering wall of the filter 7 and then the annular cavity 18, thereafter escaping via the radial outlet 9.

Then, the practitioner may interrupt aspiration and remove the canula by pulling on it axially, and then push in the piston by means of the piston rod 8a to move the piston head 8b toward the distal end 7b of the filter 7. The piston head 8b entrains bone fragments toward the distal end 7b and out of the front connector 5. The deposited bone is then expelled from the recovery device. It usually takes the form of a "core" consisting of bone moistened by the blood of the patient.

This bony material may either be reimplanted directly in the patient or deposited in a receptacle for preparation or if only part of it is to be used.

It then suffices to return the piston to its recovery position and replace the canula 12 for further use of the bone recovery function of the device, with no other demounting of parts.

The piston 8 is returned at this time to its recovery position, its travel being limited by the shoulder 1g which serves as an abutment against which the piston head 8b bears at the end of its travel.

For reasons of hygiene, the components of the recovery device, apart from the filter 7, may advantageously be made of stainless steel.

The filter 7 may be made of a material that may be sterilized and used again. Alternatively, the filter 7 may be made of plastic material, constituting an interchangeable and disposable part, used for only one patient. A bone recovery device may then be provided associated with one or more interchangeable filters each packaged in sterile packaging.

Moreover, all the components of the recovery device must be demountable in order to facilitate cleaning and/or decontaminating and/or sterilizing thereof. Thus the front connector 5 may be separated from the axial main body 1, where applicable the piston head 8b may be separated from the piston rod 8a, the pusher head 8c may be separated from the piston rod 8a, the canula 12 may be separated, the filter 7 may be separated, and where applicable the outlet tube 10 may be removed. For reasons of construction, the raised portions 11 may also be removable, being secured to the axial main body 1 by an attached part 11a.

The recovery device may also be used for placement of bone fragments directly at the implantation site by maneuvering the piston to carry out bone placement after first removing the suction canula 12.

The present invention is not limited to the embodiments that have been described explicitly and encompasses variants and generalizations thereof that fall within the scope of the following claims.

There is claimed:

1. A bone recovery device for recovering bone fragments during surgery, comprising:
    a front canula,
    an axial main body having an axial cavity passing through it with a proximal end and a distal end,
    a front connector incorporating an axial passage and adapted to be fixed to the distal end of said main body,
    a filter having a filtering wall of generally cylindrical tubular shape and adapted to be retained in position in said main body,
    an annular cavity left free around said filter between said cylindrical filtering wall of said filter and internal lateral faces of said axial main body and said front connector,
    in which device:
    said main body comprises a radial outlet communicating with said annular cavity and adapted to be connected to a suction device,
    a scraper piston is provided, having a piston rod that passes through the proximal end of said main body, and having a piston head adapted to slide axially inside said cylindrical tubular filter, said piston head blocking the proximal end of said filter at all times during use of said bone recovery device during a recovery phase and emptying said filter on axial movement in translation toward said distal end,
    the piston head being connected to the piston rod so that the piston head is moved back and forth by a first axial translation of the piston rod toward a distal end of the filter and by a second axial translation of the piston rod toward a proximal end of the filter.

2. The bone recovery device claimed in claim 1, comprising a removable front canula adapted to be fitted to said front connector to communicate with said axial passage and the interior of said filter.

3. The bone recovery device claimed in claim 1, comprising end of travel abutment means for limiting movement in translation of said piston head beyond said proximal end of said filter.

4. The bone recovery device claimed in claim 1, wherein said filter is retained, in said axial main body, by virtue of its proximal and distal end regions abutting against said axial main body and said front connector, respectively.

5. The bone recovery device claimed in claim 1, wherein the proximal end of said front connector is screwed into or onto said distal end of said axial main body.

6. The bone recovery device claimed in claim 1, wherein the diameter of said axial passage in said front connector is substantially the same as the inside diameter of said filter.

7. The bone recovery device claimed in claim 1, wherein the proximal end region of said axial main body comprises radial gripping raised portions, and said piston rod comprises a proximal pusher head.

8. The bone recovery device claimed in claim 1, comprising an outlet tube adapted to be connected to said radial outlet orifice.

9. The bone recovery device claimed in claim 1, wherein all components are demountable.

10. The bone recovery device claimed in claim 1, wherein all components, with the exception of said filter, are made of stainless steel.

11. The bone recovery device claimed in claim 1, wherein said radial outlet is adapted to be connected to a suction device.

12. The bone recovery device claimed in claim 1, associated with one or more interchangeable filters each packaged in sterile packaging.

\* \* \* \* \*